(12) United States Patent
Anich et al.

(10) Patent No.: US 11,135,138 B2
(45) Date of Patent: Oct. 5, 2021

(54) SELF-ADHESIVE DENTAL RESIN COMPOSITION AND USE THEREOF

(71) Applicant: 3M INNOVATIVE PROPERTIES COMPANY, St. Paul, MN (US)

(72) Inventors: Bernd Anich, Andechs (DE); Markus Mikulla, Andechs-Frieding (DE); Frauke Bokeloh, Graefelfing (DE); Robert F. Peez, Landsberg (DE); Rainer A. Guggenberger, Herrsching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/484,892

(22) PCT Filed: Feb. 7, 2018

(86) PCT No.: PCT/US2018/017160
§ 371 (c)(1),
(2) Date: Aug. 9, 2019

(87) PCT Pub. No.: WO2018/148238
PCT Pub. Date: Aug. 16, 2018

(65) Prior Publication Data
US 2019/0374442 A1 Dec. 12, 2019

(30) Foreign Application Priority Data
Feb. 13, 2017 (EP) ...................................... 17155813

(51) Int. Cl.
| | |
|---|---|
| *A61K 6/889* | (2020.01) |
| *A61K 6/17* | (2020.01) |
| *A61K 6/76* | (2020.01) |
| *A61K 6/77* | (2020.01) |
| *C08L 43/02* | (2006.01) |
| *A61K 6/61* | (2020.01) |

(52) U.S. Cl.
CPC ................ *A61K 6/889* (2020.01); *A61K 6/17* (2020.01); *A61K 6/76* (2020.01); *A61K 6/77* (2020.01); *A61K 6/61* (2020.01); *C08L 43/02* (2013.01)

(58) Field of Classification Search
CPC ...................................................... A61K 6/61
See application file for complete search history.

(56) References Cited

U.S. PATENT DOCUMENTS

| | | |
|---|---|---|
| 3,541,068 A | 11/1970 | Taylor |
| 4,259,075 A | 3/1981 | Yamauchi |
| 4,499,251 A | 2/1985 | Omura |
| 4,537,940 A | 8/1985 | Omura |
| 4,539,382 A | 9/1985 | Omura |
| 4,642,126 A | 2/1987 | Zador |
| 4,652,274 A | 3/1987 | Boettcher |
| 4,795,823 A | 1/1989 | Schmitt |
| 4,872,936 A | 10/1989 | Engelbrecht |
| 4,941,751 A | 7/1990 | Muehlbauer |
| 5,088,830 A | 2/1992 | Muehlbauer |
| 5,130,347 A | 7/1992 | Mitra |
| 5,530,038 A | 6/1996 | Yamamoto |
| 6,386,872 B1 | 5/2002 | Mukasa |
| 6,444,725 B1 | 9/2002 | Trom |
| 6,458,868 B1 | 10/2002 | Okada |
| 6,543,611 B1 | 4/2003 | Peuker |
| 6,730,156 B1 * | 5/2004 | Windisch ............... B82Y 30/00 106/35 |
| 6,953,535 B2 | 10/2005 | Hecht |
| 7,393,882 B2 | 7/2008 | Wu |
| 8,129,444 B2 * | 3/2012 | Hecht ........................ C09J 4/00 523/115 |
| 2004/0206932 A1 | 10/2004 | Abuelyaman |
| 2005/0252413 A1 | 11/2005 | Kangas |
| 2006/0030637 A1 | 2/2006 | Mitra |

FOREIGN PATENT DOCUMENTS

| | | | |
|---|---|---|---|
| EP | 0712622 | 5/1996 | |
| EP | 0783872 | 7/1997 | |
| EP | 1051961 | 11/2000 | |
| WO | WO-9522956 A1 * | 8/1995 | ............... A61K 6/20 |
| WO | WO 2015-006087 | 1/2015 | |

OTHER PUBLICATIONS

International Search Report for PCT International Application No. PCT/US2018/017160, dated May 9, 2018, 5 pages.

* cited by examiner

*Primary Examiner* — Michael F Pepitone
(74) *Attorney, Agent, or Firm* — Ashley M. Dreis

(57) ABSTRACT

The invention relates to a hardenable dental resin composition provided as a kit of parts comprising a powder part and a liquid part, the powder part comprising acid-reactive glass filler A, non acid-reactive nanocluster filler B, the liquid part comprising polymerizable components with an acidic moiety, polymerizable components without an acidic moiety, the hardenable dental composition further comprising a dual-cure initiator system the components of which being distributed between the powder part and the liquid part, wherein the dual-cure initiator system comprises sensitizing agent(s), oxidizing component(s), (thio)barbituric acid component(s) and transition metal component(s). The composition can be used as a self-adhesive dental resin filling material, self-adhesive dental resin core build up material, self-adhesive dental resin cement material, self-adhesive fissure sealing material, a self-adhesive dental root channel material.

20 Claims, 1 Drawing Sheet

SELF-ADHESIVE DENTAL RESIN COMPOSITION AND USE THEREOF

CROSS REFERENCE TO RELATED APPLICATIONS

This application is a national stage filing under 35 U.S.C. 371 of PCT/US2018/017160, filed Feb. 7, 2018, which claims the benefit of EP Application No. 17155813.3, filed Feb. 13, 2017, the disclosure of each of which is incorporated by reference herein in its entirety.

FIELD OF THE INVENTION

The invention relates to a self-adhesive dual-curing dental resin composition comprising as fillers an acid-reactive glass and nanoclusters.

The composition is useful in the dental field, in particular as self-adhesive dental resin core build up material, self-adhesive dental resin cement material, a dental filling material, a dental fissure sealing material, a self-adhesive dental root channel material.

BACKGROUND

To simplify the treatment process in the dental practice and in order to reduce the time needed by the practitioner to conduct a dental treatment, self-adhesive dental materials have been developed and are also commercially available on the market. These materials show good adhesion, even without a pretreatment of the tooth structure.

U.S. Pat. No. 6,953,535 B2 (Hecht et al.) describes a redox initiator system which allows dental formulations to be cured in acidic medium by way of free-radical polymerization and which ensures a high level of adhesion of the polymerized composition to the hard substance of the teeth. The redox initiator system comprises a barbituric acid or thiobarbituric acid component, a peroxo component, a sulfinic acid component and a copper component.

U.S. Pat. No. 8,129,444 (Hecht et al.) relates to a self-adhesive composition comprising ethylenically unsaturated compounds which have an acid functional group as component A, ethylenically unsaturated compounds which do not have an acid functional group, a certain amount of filling material, comprising at least one filling material that may react with component A, and initiators.

These compositions typically comprise polymerizable components with an acidic moiety and polymerizable components without an acidic moiety. Further, besides a suitable curing system, the compositions comprise filler components, which may to some extend also take part in the hardening reaction.

Besides self-adhesive bonding and cement materials there is an increasing demand for self-adhesive filling materials.

Thus, there is a need for an improved dental composition, which can be used inter alia as a self-adhesive dental filling composition.

DESCRIPTION

In particular, there is a need for a self-adhesive dual-curing hardenable dental composition which can be provided as a powder/liquid system and which shows sufficient physical properties. Further, it should be possible to produce such a composition in an easy and un-complicated manner.

Generally, it is assumed, that in order to get a sufficient material strength (e.g. flexural and/or compressive strength) and wear resistance for dental filling materials a higher content of filler is needed compared to the content of filler contained in dental bonding or cement materials. It is also assumed that using fillers having a small particle size may positively contribute to the overall mechanical performance of the composition. However, it was found that simply adding a finely divided filler may cause problems during the production process.

In particular, it has been observed, that a powder composition containing fillers having a small particle size is often difficult to handle during the production and filling process due to electrostatic charging caused by the small particles being present in the composition.

However, reducing the electrostatic charging by using production equipment made out of metal is not always possible in the dental area, as even traces of undesired metals resulting from abrasion may lead to stability issues of the compositions during storage.

Thus, in order to avoid contamination by metals, the production equipment used in the manufacturing of dental materials is often made out of plastic.

Electrostatic charging should be avoided or limited as far as possible, as it may have a negative impact on the production capacity, i.e. the number of packaging devices like dental mixing capsules which can be filled in a given time period.

Especially, if fillers were used which were surface-treated with e.g. silane components, the undesired electrostatic charging occurred.

However, to make the filler particles more compatible with the resin components, a surface-treatment of the filler particles is often needed.

Thus, there is a need for a composition which can be produced without these difficulties or showing these difficulties only at a reduced level.

In one embodiment the invention features a hardenable dental resin composition provided as a kit of parts comprising a powder part and a liquid part, the powder part comprising:
acid-reactive glass filler A, preferably in an amount from 1 to 60 wt. %,
non acid-reactive nanocluster filler B, preferably in an amount from 10 to 80 wt. %,
the liquid part comprising
polymerizable components with an acidic moiety,
polymerizable components without an acidic moiety,
the hardenable dental composition further comprising a dual-cure initiator system the components of which being distributed between the powder part and the liquid part,
wherein the dual-cure initiator system comprises:
sensitizing agent(s),
oxidizing component(s),
(thio)barbituric acid component(s) and
transition metal component(s),
wherein wt. % refers to the weight of the whole composition.

In another embodiment, the invention relates to a hardenable dental resin composition as described in the present text for use in a process comprising the steps of
providing the hardenable dental composition,
mixing the powder and liquid part of the dental composition to obtain a mixture,
applying the mixture to the surface of a tooth or a dental restoration.

The invention is also related to a kit of parts comprising the hardenable dental resin composition as described in the present text and one or more of the following components: dental adhesive, dental post and/or dental milling block.

The invention also relates to the use of the nanocluster filler described in the present text for reducing the electrical charging of powder components used for or during the production or filling process of powder compositions, in particular powder compositions for dental use.

Unless defined differently, for this description the following terms shall have the given meaning:

A "dental composition" or a "composition for dental use" or a "composition to be used in the dental field" is any composition which can and is to be used in the dental field. In this respect the composition should be not detrimental to the patients' health and thus free of hazardous and toxic components being able to migrate out of the composition. Dental compositions are typically hardenable compositions, which can be hardened at ambient conditions, including a temperature range from 15 to 50° C. or from 20 to 40° C. within a time frame of about 30 min or 20 min or 10 min or 5 min or even lower. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

A "polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (methyl)acrylate group.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i. e., $CH_2=CH-C(O)-O-$) and/or a methacryloxy group (i. e., $CH_2=C(CH_3)-C(O)-O-$).

An "ethylenically unsaturated acidic compound" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as $-COOH$ or $-CO-O-CO-$, phosphoric acid residues, such as $-O-P(O)(OH)OH$, phosphonic acid residues or sulfonic acid residues, such as $-SO_3H$.

An "initiator" is a substance being able to initiate a chemical reaction, preferably via a free radical reaction. The initiator can be a single compound or can comprise more than one component, such as a combination of a sensitizing agent with a reducing agent.

Depending on the reaction conditions chosen (e.g. pH-value >7 or pH-value <7) different initiators can be preferred.

A "redox initiator system" is defined as the combination of reducing agent(s) and oxidizing agent(s) being located on the application part of the application device. If present, transition metal component(s) are also regarded as components of the redox initiator system.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d50/µm" with regard to particle size measurement means that 50 vol. % of the particles in the analysed volume have a size below x µm. E.g., a particle size value of below 100 µm (d50) means that within the analysed volume, 50% of the particles have a size below 100 µm.

"Nano-sized particles" shall mean particles having a mean particle size in the range of 5 to 500 nm or 5 to 300 nm or 5 to 200 nm. For spherical particles, "size" refers to the diameter of the particle. For non-spherical particles, "size" refers to the so called "equivalent spherical diameter" which is the diameter of a sphere of equivalent volume.

The term "primary particle size" refers to the size of a non-associated single particle. X-ray Diffraction (XRD) is typically used to measure the primary particle size using the techniques described herein.

The term "associated" refers to a grouping of two or more primary particles that are aggregated and/or agglomerated. Similarly, the term "non-associated" refers to two or more primary particles that are free or substantially free from aggregation and/or agglomeration.

The term "aggregation" refers to a strong association of two or more primary particles. For example, the primary particles may be chemically bound to one another. The breakdown of aggregates into smaller particles (e.g., primary particles) is generally difficult to achieve.

Aggregated fillers are commercially available e.g. from Degussa, Cabot Corp or Wacker under the product designation Aerosil™, CAB-O-SIL™ and HDK (e.g. fumed or pyrogenic silica).

"Non-aggregated filler" means that the filler particles are present in a discrete, un-associated (i.e. non-agglomerated and non-aggregated) stage. If desired this can be proven by TEM microscopy. However, unavoidable traces of small amounts of agglomerated or aggregated particles (e.g. up to about 1% compared to the amount of non-aggregated filler) may still be there.

Non-aggregated nano-sized silicas are commercially available e.g. from Nalco Chemical Co. (Naperville, Ill.) under the product designation NALCO COLLOIDAL SILICAS e.g. NALCO products #1040, 1042, 1050, 1060, 2327 and 2329. Non-aggregated fillers are used and described e.g. in U.S. Pat. No. 7,393,882 (3M).

The term "agglomeration" refers to a weak association of two or more primary particles. For example, the primary particles may be held together by charge or polarity. The breakdown of agglomerates into smaller particles (e.g., primary particles) is less difficult than the breakdown of aggregates into smaller particles.

Agglomerated nano-sized particles are typically present in the form of clusters. The respective fillers are also referred to as nanoclusters.

A "solvent" means a liquid which is able to at least partially disperse or dissolve a component at ambient conditions (e.g. 23° C.). A solvent typically has a viscosity below about 10 or below about 8 or below about 6 Pa*s.

"Glass ionomer cement" or "GIC" shall mean a cement curing or hardening by the reaction between an acid-reactive glass and a polyacid in the presence of water.

"Resin modified glass ionomer cement" or "RM-GIC" shall mean a GIC containing in addition radically polymerizable component(s), an initiator system and typically 2-hydroxyl-ethyl-methacrylate (HEMA).

"Acid-reactive filler" shall mean a filler that chemically reacts in the presence of an acidic component.

"Non acid-reactive filler" shall mean a filler, which does not show a chemical reaction within 6 min at all, if mixed with a (poly)acid or which shows only a reduced (i.e. time-delayed) reaction.

To distinguish an acid-reactive filler from a non acid-reactive filler the following test can or is to be conducted:

A composition is prepared by mixing Part A with Part B in a mass ratio of 2 to 1, wherein:

Part A contains: filler to be analysed: 100 wt. %.

Part B contains: poly (acrylic acid co maleic acid) (Mw: about 18,000+/−3,000): 43.6 wt. %, water: 47.2 wt. %, tartaric acid: 9.1 wt. %, benzoic acid: 0.1 wt. %.

The filler is characterized as non-acid reactive, if within 6 min after preparing the above composition the shear stress is less than 50,000 Pa, if determined by conducting an oscillating measurement using a rheometer by applying the following conditions: using an 8 mm plate, 0.75 mm gap, at 28° C., frequency: 1.25 Hz, deformation: 1.75%.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer. The composition described in the present text does typically not contain a polyacid.

"Complexing agent" or "chelating agent" shall mean a low molecular agent comprising moieties and being able to form a complex with metal ions like calcium or magnesium; e.g. tartaric acid. The terms "complexing agent" and "chelating agent" are interchangeable. The composition described in the present text does typically not contain a complexing agent like tartaric acid, if added as a separate component.

As used herein, "hardening" or "curing" a composition are used interchangeably and refer to polymerization and/or crosslinking reactions including, for example, photopolymerization reactions and chemical polymerization techniques (e. g., ionic reactions or chemical reactions forming radicals effective to polymerize ethylenically unsaturated compounds) involving one or more materials included in the composition.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

As used herein, a "dental surface" refers to tooth structures (e. g., enamel, dentin, and cementum) and bone.

A "self-etching" composition refers to a composition which bonds to a dental surface without pre-treating the dental surface with an etchant. Preferably, a self-etching composition can also function as a self-adhesive primer wherein no separate etchant or primer is used.

A "self-adhesive" composition refers to a composition that is capable of bonding to a dental surface without pre-treating the dental surface with a primer or bonding agent. Preferably, a self-adhesive composition is also a self-etching composition wherein no separate etchant is used.

A "self-curing composition" means a composition which cures by a redox-reaction without application of radiation.

An "untreated" dental surface refers to a tooth or bone surface that has not been treated with an etchant, primer, conditioner, or bonding agent prior to application of a self-etching adhesive or a self-adhesive composition.

An "unetched" dental surface refers to a tooth or bone surface that has not been treated with an etchant prior to application of a self-etching adhesive or a self-adhesive composition.

A composition is "essentially or substantially free of" a certain component, if the composition does not contain said component as an essential feature. Thus, said component is not willfully added to the composition either as such or in combination with other components or ingredient of other components.

A composition being essentially free of a certain component usually contains the component in an amount of less than about 1 wt. % or less than about 0.5 wt. % or less than about 0.1 wt. % or less than about 0.01 wt. % with respect to the whole composition or material. The composition may not contain the said component at all. However, sometimes the presence of a small amount of the said component is not avoidable e.g. due to impurities contained in the raw materials used.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

The term "comprise" shall include also the terms "consist essentially of" and "consists of".

DETAILED DESCRIPTION

Figure 1:
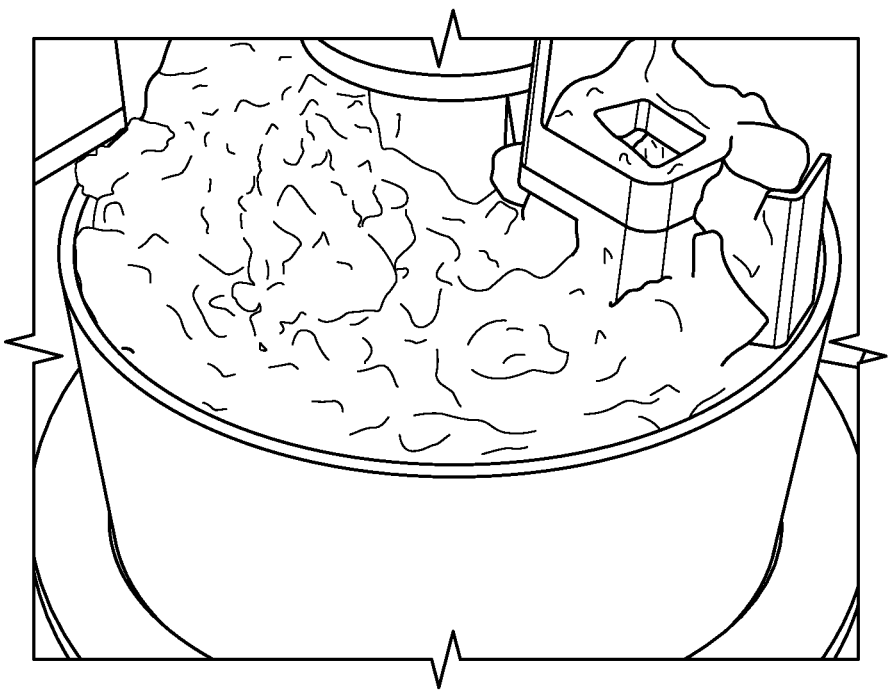
FIG. 1 is a photograph of a vessel used for filling a powder mixture containing non-reactive glass filler into a packaging device.

Surprisingly it was found, that the extent of electrostatic charging of the powder components during the production process of powder compositions can be reduced, when an agglomerated nano filler (i.e. nanocluster filler) was used.

Further, it was found that the hardenable dental resin composition described in the present text shows improved physical properties like flexural strength after hardening.

In certain embodiments the hardenable dental resin composition described in the present text fulfils one or more, sometimes all of the following properties once the components of the powder part and the liquid part are mixed:

Setting time: within 5 or 4 or 3 min determined according to EN-ISO 9917-1:2007; Working time: within 4 or 3 or 2 or 1 min determined according to EN-ISO 9917-1:2007.

If desired, the setting time and curing behaviour can be determined as described in more detail in the Example section below.

The composition described in the present text typically has a sufficient working time allowing the practitioner not only to adequately mix the composition but also to apply the composition to a cavity or the surface of a crown, bridge, root canal, fissure or prepared tooth.

Further, the composition described in the present text has an adequate setting time, which is time saving for the practitioner and convenient for the patient.

The dental resin composition obtained or obtainable by mixing the two parts of the curable dental composition described in the present text typically fulfils at least one or more or sometimes all of the following parameters after hardening:

Flexural strength: above 70 or above 80 MPa or above 90 MPa, if determined according to ISO 4049/2009(E);

Compressive strength: above 200 or above 250 or above 300 MPa, if determined according to EN-ISO 9917-1/2007 with the proviso that for covering the composition a glass slab is used instead of a foil.

If desired, these parameters can be determined as described in the Example section below.

The hardenable dental resin composition described in the present text is provided as a kit of parts comprising a powder part and a liquid part.

The mixing ratio of powder part to liquid part is typically from 6:1 to 1:1 with respect to weight, or from 4:1 to 1:1 or from 2:1 to 1:1.

A ratio outside this range might negatively affect physical properties of the hardened composition such as flexural strength.

The powder part comprises acid-reactive glass filler A and non acid-reactive nanocluster filler B.

The powder part may optionally comprise one or more of the following components:

oxidizing component(s),
(thio)barbituric acid component(s),
sulfinic acid component(s),
sensitizer,
transition metal component(s) and
additive(s).

The powder part contains acid-reactive glass filler(s) as filler A.

The nature and structure of the acid-reactive glass filler A is not particularly limited, either unless the desired result cannot be achieved.

According to one embodiment, the acid-reactive glass filler can be characterized by at least one or more or all of the following parameters:

Mean particle size: about 3 to about 10 μm;
(d10/μm): from 0.5 μm to 3 μm; (d50/μm): from 2 μm to 7 μm; (d90/μm): from 6 μm to 15 μm.

If the mean particle size of the acid-reactive glass filler is above the range outlined above, the consistency of the composition obtained when mixing the compositions contained in the kit of parts described in the present text might not be adequate and the desired mechanical properties might be negatively affected.

Typical acid-reactive glasses include aluminosilicate glasses and in particular fluoroaluminosilicate ("FAS") glasses.

FAS glasses are particularly preferred. The FAS glass typically contains a sufficient amount of elutable cations so that a hardened dental composition can be obtained when the glass is mixed with the other components of the hardenable composition.

The FAS glass also typically contains a sufficient amount of elutable fluoride ions so that the hardened composition may have cariostatic properties.

The glass can be made from a melt containing fluoride, silica, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Suitable FAS glasses will be familiar to those skilled in the art, and are available from a wide variety of commercial sources, and many are found in currently available glass ionomer cements such as those commercially available under the trade designations Ketac™ Molar or Ketac™ Fil Plus (3M Oral Care), Ketac™ Universal (3M Oral Care) and FUJI™ IX (GC Dental Industrial Corp., Tokyo, Japan).

Fluoroaluminosilicate glasses can be prepared by fusing mixtures of silica, alumina, cryolite and fluorite.

Useful acid-reactive inorganic glasses can also be characterized by the Si/Al ratio. Fillers having a Si/Al ratio (by wt. %) of below 1.5 or 1.4 or 1.3 were found to be useful.

Suitable acid-reactive inorganic fillers are also commercially available from e.g. Schott AG (Germany) or Speciality Glass (US).

Mixtures of acid-reactive glass fillers can be used, if desired.

The acid-reactive glass filler A is typically present in the following amount:

Lower limit: at least 1 or at least 5 or at least 10 wt. %;
Upper limit: utmost 60 or utmost 55 or utmost 50 wt. %;
Range: from 1 to 60 or from 5 to 55 or from 10 to 50 wt. %;
wt. % with respect to the whole composition.

The powder part contains nanocluster filler B, comprising non acid-reactive agglomerated nano particles.

The nano-sized particles of filler B are non-acid reactive. That is, the particles do not cure in a glass ionomer cement reaction, if combined with a polyacid in the presence of water.

Suitable nanocluster filler B can typically be characterized by at least one or all of the following features:
Specific surface (BET): from 50 to 400 or 60 to 300 or from 80 to 250 $m^2/g$;
Average particle diameter of primary particles: from 5 to 100 nm or 10 to 50 or 12 to 40 nm;
comprising particles of $SiO_2$, $ZrO_2$ and mixtures thereof.

If desired, the specific surface can be determined according to Brunauer, Emmet and Teller (BET) by using a device (Monosorb) available from Quantachrome.

If desired, the mean particle size can be determined by light scattering using e.g. a Malvern Mastersizer 3000 device available from Malvern Instruments.

Nanocluster filler B can be produced according to the processes described e.g. U.S. Pat. No. 6,730,156 B1 (Windisch et al.).

Nanocluster filler B can be prepared from a suitable sol and one or more oxygen containing heavy metal compound solution(s) precursors which may be salts, sols, solutions, or nano-sized particles; of these, sols are preferred. For purposes of this invention, a sol is defined as a stable dispersion of colloidal solid particles within a liquid. The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc. Factors that will guide the choice of the sol depends on the combination of the following properties: a) the average size of the individual particles, which is preferably less than 100 nm in diameter, b) the acidity: the pH of the sol should be preferably below 6 and more preferably below 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability.

If the starting sol is basic, it should be acidified e.g. by addition of nitric or other suitable acid to decrease the pH. However, choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio range of non-heavy metal oxide ("non-HMO") to heavy metal oxide ("HMO"), expressed as non-HMO:HMO is 0.5:1 to 10:1, more preferably 3:1 to 9:1, and most preferable 4:1 to 7:1.

In one embodiment where the aggregated nano-sized particles contain silica and zirconium containing compounds, the method of preparation starts with a mixture of silica sol and zirconyl acetate, at about a 5.5:1 molar ratio.

Prior to mixing the non-heavy metal oxide sol with the heavy metal oxide precursor, the pH of the non-heavy metal oxide sol is preferably reduced to provide an acidic solution having a pH of 1.5 to 4.0.

The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying.

The resulting dried material is preferably made up of small substantially spherical particles as well as broken hollow spheres. These fragments are then batch calcined to further remove residual organics. The removal of the residual organics allows the filler to become more brittle, which results in more efficient particle size reduction. During calcining, the soak temperature is preferably set at 200° C. to 800° C., more preferably 300° C. to 600° C. Soaking is performed for 0.5 hours to 8 hours, depending on the amount of material being calcined. It is preferred that the soak time of the calcine step be such that a plateaued surface area is obtained. It is preferred that the time and temperature be chosen such that the resulting filler is white in color, free from black, grey, or amber colored particles, as determined by visual inspection.

The calcined material is then preferably milled to a median particle size of less than 5 μm, preferably less than 2 μm (on a volumetric basis), as can be determined by using a Sedigraph 5100 (Micrometrics, Norcross, Ga.). The particle size determination can be performed by first obtaining the specific density of the filler using an Accuracy 1330 Pycometer (Micrometrics, Norcross, Ga.). Milling can be accomplished by various methods including for example, stirred milling, vibratory milling, fluid energy milling, jet milling and ball milling. Ball milling is the preferred method. If desired, the nano-sized particles can be surface treated.

According to one embodiment, the surface treatment is done with silane containing component(s). Surface treating agents with and without reactive moieties can be used.

Examples of surface treating agents without a reactive moiety include methyltrimethoxysilane, dimethyldimethoxysilane, phenyltrimethoxysilane, methyltriethoxysilane, dimethyldiethoxysilane, phenyltriethoxysilane, hexyltrimethoxy-silane, octyltriethoxysilnae, decyltriethoxysilane, etc.

Examples of surface treating agents with a reactive moiety include 3-methacryl-oxypropyltrimethoxysilane (MPTS), 8-methacryloyloxyoctyl trimethoxysilane, 9-methacryloyloxynonyl trimethoxysilane, 10-methacryloyloxydecyl trimethoxysilane, 11-methacryloyloxyundecyl trimethoxysilane, 11-methacryloyloxyundecyl dichloromethylsilane, 11-methacryloyloxyundecyl trichlorosilane, 11-methacryloyloxyundecyl dimethoxymethylsilane, 12-methacryloyloxydodecyl trimethoxysilane, 13-methacryloyloxytridecyl trimethoxysilane, and the like.

The non acid-reactive nanocluster filler B is typically present in the following amount:
Lower limit: at least 10 or at least 15 or at least 18 wt. %;
Upper limit: utmost 80 or utmost 75 or utmost 70 wt. %;
Range: from 10 to 80 or from 15 to 75 or from 18 to 70 wt. %;
wt. % with respect to the whole composition.

According to one embodiment, the non acid-reactive nanocluster filler B is used in excess with respect to weight compared to the acid-reactive glass filler A.

Either the powder part or the liquid part contains oxidizing component(s).

The nature and structure of the oxidizing component(s) is not particularly limited unless the desired result cannot be achieved.

Suitable oxidizing components include peroxides, peroxodisulfate, peroxodiphosphate and mixtures thereof.

Generally all peroxide(s), i.e. inorganic and organic peroxides, which can be incorporated in a powder composition can be used.

In contrast to inorganic peroxides, organic peroxide(s) do not comprise metals or metal ions. Thus, organic peroxides typically only comprise C, O, H and optionally halogens (e.g. F, Cl, Br).

Organic peroxides which can be used include ketone peroxide(s), diacyl peroxide(s), dialkyl peroxide(s), peroxyketal(s), peroxyester(s) and peroxydicarbonate(s).

According to one embodiment, the organic peroxide is a di-peroxide, preferably a di-peroxide comprising the moiety $R_1$—O—O—$R_2$—O—O—$R_3$, with $R_1$ and $R_3$ being independently selected from H, alkyl (e.g. $C_1$ to $C_6$), branched alkyl (e.g. $C_1$ to $C_6$), cycloalkyl (e.g. $C_5$ to $C_{10}$), alkylaryl (e.g. $C_7$ to $C_{12}$) or aryl (e.g. $C_6$ to $C_{10}$) and $R_2$ being selected from alkyl (e.g. ($C_1$ to $C_6$) or branched alkyl (e.g. $C_1$ to $C_6$).

Examples of ketone peroxides include methyl ethyl ketone peroxide, methyl isobutyl ketone peroxide, methyl cyclohexanone peroxide, and cyclohexanone peroxide.

Examples of peroxyesters include 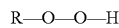-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate and t-butylperoxymaleic acid.

Examples of peroxidicarbonates include di-3-methoxy peroxidicarbonate, di-2-ethylhexyl peroxydicarbonate, bis(4-t-butylcyclohexyl)peroxidicarbonate, diisopropyl-1-peroxydicarbonate, di-n-propyl peroxidicarbonate, di-2-ethoxyethyl-peroxidicarbonate, and diallyl peroxidicarbonate.

Examples of diacyl peroxides include acetyl peroxide, benzoyl peroxide, decanoyl peroxide, 3,3,5-trimethylhexanoyl peroxide, 2,4-dichlorobenzoyl peroxide and lauroylperoxide.

Examples of dialkyl peroxides include di-t-butyl peroxide, dicumylperoxide, t-butylcumyl peroxide, 2,5-dimethyl-2,5-di(t-butylperpoxy)hexane, 1,3-bis(t-butylperoxyisopropyl)benzene and 2,5-dimethyl-2,5-di(t-butylperoxy)-3-hexane.

Examples of peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butylester.

According to one embodiment, the organic peroxide is a hydroperoxide, in particular a hydroperoxide comprising the structural moiety:

R—O—O—H with R being (e.g. $C_1$ to $C_{20}$) alkyl, (e.g. $C_3$ to $C_{20}$) branched alkyl, (e.g. $C_6$ to $C_{12}$) cycloalkyl, (e.g. $C_7$ to $C_{20}$) alkylaryl or (e.g. $C_6$ to $C_{12}$) aryl.

Examples of suitable organic hydroperoxides include t-butyl hydroperoxide, t-amyl hydroperoxide, p-diisopropylbenzene hydroperoxide, cumene hydroperoxide, pinane hydroperoxide, p-methane hydroperoxide and 1,1,3,3-tetramethylbutyl hydroperoxide.

The peroxide(s) are sometimes used in combination with activator(s).

Suitable as activators are, for example, tertiary aromatic amines, such as the N,N-bis-(hydroxyalkyl)-3,5-xylidines known from U.S. Pat. No. 3,541,068 as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Suitable peroxodisulfate components and/or peroxodiphosphate components and/or mixtures thereof, which can be used include organic and/or inorganic components.

Suitable examples include ammonium, sodium, and potassium peroxodisulfate components and/or peroxodiphosphate components. Sodium peroxodisulfate is sometimes preferred For further acceleration, the polymerization is preferably carried out in the presence of transition metal compounds.

The oxidizing component is typically present in the following amount:

Lower limit: at least 0.1 or at least 0.2 or at least 0.5 wt. %;

Upper limit: utmost 10 or utmost 8 or utmost 5 wt. %;

Range: from 0.1 to 10 or from 0.2 to 8 or from 0.5 to 5 wt. %;

wt. % with respect to the whole composition.

The dental resin composition described in the present text contains (thio)barbituric acid component(s).

The nature and structure of the (thio)barbituric acid component(s) is not particularly limited, either unless the desired result cannot be achieved.

Suitable (thio)barbituric acid components have the general structure:

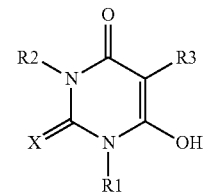

In this structure R1, R2, and R3, which may be identical or different, are independently selected from the following: hydrogen, alkyl, substituted alkyl, alkenyl, cycloalkyl, substituted cycloalkyl, arylalkyl, aryl or substituted aryl radical. R1, R2, and R3 may also incorporate a halogen radical such as chloro or a hydroxyl, amino or nitro group.

If one of the radicals R1 to R3 is unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals include methyl, ethyl, propyl, isopropyl, n-butyl, t-butyl, isobutyl, n-pentyl, and isoamyl.

If one of the radicals R1 to R3 is a substituted alkyl radical then the alkyl moiety of this radical typically has the number of carbon atoms indicated above for unsubstituted alkyl. If one of the radicals R1 to R3 is alkoxyalkyl or alkoxycarbonylalkyl then the alkoxy radical typically contains, for example, from 1 to 5 carbon atoms and is most typically methyl, ethyl, propyl, isopropyl, n-butyl, t-butyl, isobutyl, n-pentyl or isoamyl. If one of the radicals R1 to R3 is haloalkyl then the halo moiety is understood to be fluoro, chloro, bromo or iodo.

If one of the radicals R1 to R3 is alkenyl, it is typically a $C_3$ to $C_5$ alkenyl radical, especially allyl.

If one of the radicals R1 to R3 is unsubstituted cycloalkyl, it is typically a $C_4$ to $C_7$ cycloalkyl radical, such as cyclopentyl or cyclohexyl. If one of the radicals R1 to R3 is a substituted cycloalkyl then it is typically one of the above-indicated cycloalkyl radicals, with the substituent or substituents on the cycloalkyl radical possibly being, for example, $C_1$ to $C_4$ alkyl such as methyl, ethyl, propyl, n-butyl or isobutyl, fluoro, chloro, bromo, iodo or $C_1$ to $C_4$ alkoxy, especially methoxy. If one of the radicals R1 to R3 is aryl or aralkyl, then it is typically a phenyl or naphthyl as aryl. Particularly suitable arylalkyl radicals are benzyl and phenylethyl.

R1 to R3 may also be substituted aryl radicals if desired. In this case phenyl and naphthyl are preferred and as ring substituents $C_1$ to $C_4$ alkyl, especially methyl, halogen or $C_1$ to $C_4$ alkoxy, especially methoxy.

X is oxygen or sulfur.

Suitable (thio)barbituric acid component(s) include barbituric acid, thiobarbituric acid, 1,3,5-trimethylbarbituric acid, 1-phenyl-5-benzylbarbituric acid, 1-benzyl-5-phenylbarbituric acid, 1,3-dimethylbarbituric acid, 1,3-dimethyl-5-phenylbarbituric acid, 1-cyclohexyl-5-ethylbarbituric acid, 5-laurylbarbituric acid, 5-butylbarbituric acid, 5-allylbarbituric acid, 5-phenylthiobarbituric acid, 1,3-dimethylthiobarbituric acid, trichlorobarbituric acid, 5-nitrobarbituric acid, 5-aminobarbituric acid, and 5-hydroxybarbituric acid and mixtures thereof.

The (thio)barbituric acid component is typically present in the following amount:

Lower limit: at least 0.1 or at least 0.2 or at least 0.5 wt. %;
Upper limit: utmost 5 or utmost 4 or utmost 3 wt. %;
Range: from 0.1 to 5 or from 0.2 to 4 or from 0.3 to 3 wt. %;
wt. % with respect to the whole composition.

The powder part may also comprise a sulfinic acid component as part of the redox initiator system. The sulfinic acid component may function as a reducing agent.

According to one embodiment the sulfinic acid component and/or mixtures thereof has the general formula R1SOO—R2, in which R1 is an alkyl, substituted alkyl, alkenyl, cycloalkyl, substituted cycloalkyl, arylalkyl, aryl or substituted aryl radical and R2=H, metal such as lithium, sodium or potassium or is an alkyl, substituted alkyl, alkenyl, cycloalkyl, substituted cycloalkyl, arylalkyl, aryl or substituted aryl radical.

If one of the radicals R1 or R2 is unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals are methyl, ethyl, propyl, isopropyl, n-butyl, t-butyl, isobutyl, n-pentyl, and isoamyl.

If one of the radicals R1 or R2 is a substituted alkyl radical then the alkyl moiety of this radical typically has the number of carbon atoms indicated above for unsubstituted alkyl. If one of the radicals R1 or R2 is alkoxyalkyl or alkoxycarbonylalkyl then the alkoxy radical contains, for example, from 1 to 5 carbon atoms and is preferably methyl, ethyl, propyl, isopropyl, n-butyl, t-butyl, isobutyl, n-pentyl or isoamyl. If one of the radicals R1 or R2 is haloalkyl, then the halo moiety is understood to be fluoro, chloro, bromo or iodo.

If one of the radicals R1 or R2 is alkenyl, then it is typically a $C_3$ to $C_5$ alkenyl radicals, especially allyl.

If one of the radicals R1 or R2 is unsubstituted cycloalkyl, then it is typically $C_4$ to $C_7$ cycloalkyl radicals, such as cyclopentyl or cyclohexyl.

If one of the radicals R1 or R2 is substituted cycloalkyl, then it is typically one of the above-indicated cycloalkyl radicals, with the substituent or substituents on the cycloalkyl radical possibly being, for example, $C_1$ to $C_4$ alkyl such as methyl, ethyl, propyl, n-butyl or isobutyl, fluoro, chloro, bromo, iodo or $C_1$ to $C_4$ alkoxy, especially methoxy.

If one of the radicals R1 or R2 is aryl or aralkyl, then it is typically a phenyl or naphthyl as aryl. Preferred arylalkyl radicals include benzyl and phenylethyl.

R1 or R2 may also be substituted aryl radicals if desired. In this case phenyl and naphthyl are preferred and as ring substituents $C_1$ to $C_4$ alkyl, especially methyl, halogen or $C_1$ to $C_4$ alkoxy, especially methoxy.

Representatives of the sulfinic acid components also include salts of sulfinic acid, including sodium, potassium and ammonium salts.

Specific examples of sulfinic acid components include benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

Particularly suitable sulfinic acid component are sodium toluenesulfinate or sodium benzenesulfinate and their hydrates.

If present, the sulfinic acid component is typically present in the following amount:

Lower limit: at least 0.1 or at least 0.2 or at least 0.5 wt. %;
Upper limit: utmost 5 or utmost 4 or utmost 3 wt. %;
Range: from 0.1 to 5 or from 0.2 to 4 or from 0.3 to 3 wt. %;
wt. % with respect to the whole amount of the composition.

The liquid part comprises polymerizable component(s) with an acidic moiety and polymerizable component(s) without an acidic moiety.

The liquid part may optionally comprise one or more of the following components:
sensitizing agent(s),
transition metal component(s),
solvent(s) and
additive(s).

The liquid part contains polymerizable component(s) with at least one acidic moiety.

The nature and structure of the polymerizable components with an acidic moiety is not particularly limited, unless the desired result cannot be achieved.

Examples of the acidic moiety include carboxylic acid residues, phosphoric acid residues, phosphonic acid residues, or sulfonic acid residues.

In one embodiment, the polymerizable component having an acidic moiety can be represented by the following formula $A_nBC_m$ B being a backbone group, such as (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, A being an ethylenically unsaturated group attached to the backbone group, such as a (meth)acryl moiety, C being an acidic group attached to the backbone group, with m, n=1, 2, 3, 4, 5 or 6, wherein the acidic group comprises one or more carboxylic acid residues, such as —COOH or —CO—O—CO—, phosphoric acid residues, such as —O—P(O)(OH)OH, phosphonic acid residues, such as —P(O)(OH)OH or sulphonic acid residues, such as —SO$_3$H.

Specific examples of ethylenically unsaturated acidic compounds include, but are not limited to glycerol phosphate mono(meth)acrylates, glycerol phosphate di(meth)acrylates, hydroxyethyl (meth)acrylate phosphates, bis glycerol phosphate di(meth)acrylates, bis glycerol phosphate tetra(meth)acrylates bis((meth)acryloxyethyl) phosphate, ((meth)acryloxypropyl) phosphate, bis((meth)acryloxypropyl) phosphate, bis((meth)acryl-oxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis ((meth)acryloxydecyl) phosphate, caprolactone methacrylate phosphate, di or tri(meth)acrylated citric acid, poly (meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, and the like. Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids or polycarboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example in US 2004/0206932 A1 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Fuchigami et al.) and EP 1 051 961 A1 (Hino et al.).

Typical compositions also include an ethylenically unsaturated acidic compound with at least one phosphoric acid group (e.g. P—OH moiety).

Examples of preferred phosphoric acid group-containing polymerizable monomer include the mono- and diesters of phosphoric acid with glycerine di(meth)acrylate, 2-(meth)acryloyloxyethyl dihydrogenphosphate, bis[2-(meth)acryloyloxyethyl] hydrogenphosphate, 2-(meth)acryloyloxyethylphenyl hydrogenphosphate, bis[6-(meth)acryloyloxyhexyl]hydrogenphosphate, 6-(meth)acryloyloxyhexyl dihydrogenphosphate, 6-(meth)acryloyloxyhexylphenyl hydrogenphosphate, 10-(meth)acryloyloxydecyl dihydrogenphosphate, bis[10-(meth)acryloyloxydecyl] hydrogenphosphate, 1,3-di(meth)acryloyloxypropane-2-dihydrogenphosphate, 1,3-di(meth)-acryloyloxy-propane-2-phenyl hydrogenphosphate, and bis[5-{2-(meth)acryloyloxyethoxy-carbonyl} heptyl] hydrogenphosphate, diphosphoric acid-P,P'-di-hydroxyethyl (meth)acrylate ester and mixtures thereof.

The polymerizable components with an acidic moiety is typically present in the following amount:
Lower limit: at least 1 or at least 5 or at least 8 wt. %;
Upper limit: utmost 30 or utmost 25 or utmost 20 wt. %;
Range: from 1 to 30 or from 5 to 25 or from 8 to 20 wt. %;
wt. % with respect to the whole composition.

The liquid part contains polymerizable component(s) without an acidic moiety.

The nature and structure of the polymerizable components without an acidic moiety is not particularly limited, either unless the desired result cannot be achieved.

The polymerizable component(s) without acidic moiety(s) is typically a free-radically polymerizable material, including ethylenically unsaturated monomer, monomers or oligomers or polymers.

Suitable polymerizable component(s) without acidic moiety(s) can be characterized by the following formula:

$A_nBA_m$ with A being an ethylenically unsaturated group attached to backbone B, such as a (meth)acryl moiety, B being selected from (i) linear or branched $C_1$ to $C_{20}$ or $C_2$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), or (iii) organic group having 4 to 20 carbon atoms bonded to one another by one or more ether, thioether, ester, thioester, thiocarbonyl, amide, urethane, carbonyl and/or sulfonyl linkages, m, n being independently selected from 0, 1, 2, 3, 4, 5 or 6 with the proviso that n+m is greater 0, that is that at least one A group is present.

Such polymerizable materials include mono-, di- or polyacrylates and methacrylates and alpha-omega diol-di(meth)acrylates of $C_2$ to $C_{20}$ alkanes, such as methyl (meth)acrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol di(meth)acrylate, 1,3-propanediol di(meth)acrylate, 1,4-butanediol-di(meth)acrylate, 1,6-hexanediol-di(meth)acrylate, 1,10-decanediol-di(meth)acrylate, 1,12-dodecane-di(meth)acrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetra(meth)acrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-acryloxy-2-hydroxy)]-p-propoxyphenyldimethylmethane and trishydroxyethyl-isocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used, if desired.

Further polymerizable components which may be present include di(meth)acrylates of ethoxylated bis-phenol A, for example 2,2'-bis(4-(meth)acryl-oxytetraethoxyphenyl)propanes, 2,2'-bis(4-(meth)acryloxytriethoxyphenyl)propanes, 2,2'-bis(4-(meth)acryloxydiethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826, such as bis[3 [4]-methacryl-oxymethyl-8 (9)-tricyclo[5.2.1.0$^{2,6}$]decylmethyl triglycolate. Suitable are also 2,2-bis-4(3-methacryloxy-2-hydroxypropoxy)phenyl-propane (Bis-GMA), 2,2-bis-4(3-methacryloxypropoxy) phenylpropane, 7,7,9-trimethyl-4,13-dioxo-3,14-dioxa-5, 12-diazahexadecane-1,16-dioxy dimethacrylate (UDMA), urethane (meth)acrylates and di(meth)acrylates of bishydroxymethyltricyclo-(5.2.1.0$^{2,6}$)decane.

Further examples for polymerizable component(s) without an acidic moiety are the dimethycrylate and the diacrylate derived from tricyclodecan-dimethanol (mixture of isomers) ("T-Acrylat", "T-Methacrylat").

These ethylenically unsaturated monomers can be employed in the dental composition(s) either alone or in combination with the other ethylenically unsaturated monomers. In addition or besides those components, other hardenable components which can be added include oligomeric or polymeric compounds, such as polyester (meth)acrylates, polyether (meth)acrylates, polycarbonate (meth)acrylates and polyurethane (meth)acrylates. The molecular weight of these compounds is typically less than 20,000 g/mol, particularly less than 15,000 g/mol and in particular less than 10,000 g/mol.

Polymerizable monomers comprising a hydroxyl moiety and/or a 1,3-diketo moiety can also be added. Suitable compounds include 2-hydroxyethyl (meth)acrylate (HEMA), 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono (meth)acrylate, and further 1,2- or 1,3- and 2,3-dihydroxypropyl (meth)acrylate, 2-hydroxypropyl-1,3-di(meth)acrylate, 3-hydroxypropyl-1,2-di(meth)acrylate, N-(meth) acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy-2-hydroxypropyl (meth)acrylate, bisphenol A diglycidyl (meth)acrylate and the like. 2-Hydroxyethyl (meth)acrylate, 2-hydroxypropyl (meth) acrylate and 2,3-dihydroxypropyl (meth)acrylate are particularly preferable.

The polymerizable components without an acidic moiety is typically present in the following amount:
Lower limit: at least 1 or at least 5 or at least 8 wt. %;
Upper limit: utmost 40 or utmost 30 or utmost 20 wt. %;
Range: from 1 to 40 or from 5 to 30 or from 8 to 20 wt. %;
wt. % with respect to the whole composition.

The dental resin composition described in the present text contains sensitizing agent(s).

The sensitizing agent(s) is typically present in the liquid part.

Alternatively, the sensitizing agent(s) may be present in the powder part or be present in the liquid part and the powder part.

The nature and structure of the sensitizing agent is not particularly limited unless the intended purpose is not negatively affected.

By incorporating a sensitizing agent, a composition is obtained which can be characterized as "dual curing", that is, it contains a redox-initiator system which is suitable to harden the composition without radiation ("dark-curing or self-curing") and a sensitizing agent which is suitable to harden the composition upon the application of radiation ("light curing").

Suitable sensitizing agent for free radical polymerization are generally known to the person skilled in the art dealing with dental materials.

As the sensitizing agent, those which can polymerize the polymerizable monomer(s) by the action of a visible light having a wavelength of from 390 nm to 830 nm are preferred.

Suitable sensitizing agents often contain an alpha di-keto moiety, an anthrachinone moiety, a thioxanthone moiety or benzoin moiety.

Examples of sensitizing agents include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylamino-phenyl)ketone, 4,4,'-bisdiethylaminobenzophenone.

Typical photoinitiator systems comprise a combination of a sensitizing agent and a reducing agent.

As the reducing agent, tertiary amines and the like are generally used.

Suitable examples of the tertiary amines include N,N-dimethyl-p-toluidine, N,N-dimethylaminoethyl methacrylate, triethanolamine, methyl 4-dimethylaminobenzoate, ethyl 4-dimethylaminobenzoate, methyldiphenylamine and isoamyl 4-dimethylaminobenzoate. These compounds may be used singly or in admixture.

The sensitizing agent is typically present in the following amount:
Lower limit: at least 0.005 or at least 0.01 or at least 0.02 wt. %;
Upper limit: utmost 2 or utmost 1 or utmost 0.5 wt. %;
Range: from 0.005 to 2 or from 0.01 to 1 or from 0.02 to 0.5 wt. %;
wt. % with respect to the whole composition.

The dental resin composition described in the present text contains a transition metal component. The transition metal component can be present in the liquid part.

Alternatively, the transition metal component(s) can be present in the powder part or be present in the liquid part and the powder part.

For storage stability reasons, it can sometimes be preferred to add the transition metal component(s) to the powder part.

The nature and structure of the transition metal component(s) is not particularly limited, either unless the desired result cannot be achieved.

Suitable transition metal component(s) include organic and/or inorganic salt(s) from titanium, vanadium, chromium, manganese, iron, cobalt, nickel, and/or copper, with copper and iron being sometimes preferred.

According to one embodiment, the transition metal component comprises a copper component. The oxidation stage of copper in the copper component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper procetonate), copper salicylate complexes of copper with thiourea, ethylenediaminetetraacetic acid and/or mixtures thereof. The copper compounds can be used in hydrated form or free of water. Especially preferred is copper acetate.

The transition metal component(s) is typically present in the following amount:
    Lower limit: at least 0.001 or at least 0.005 or at least 0.01 wt. %;
    Upper limit: utmost 1 or utmost 0.8 or utmost 0.5 wt. %;
    Range: from 0.001 to 1 or from 0.005 to 0.8 or from 0.01 to 0.5 wt. %;
wt. % with respect to the whole composition.

The liquid part may optionally contain solvent(s).

Adding solvent(s) or co-solvent(s) may help to adjust the viscosity and consistency of the composition.

Examples of solvent(s) which can be used include alcohols (e.g. methanol, ethanol, propanol), polyalcohols/polyols (e.g. ethylene glycol, glycerol) and mixtures thereof.

The hardenable dental resin composition described in the present text may contain in addition additive(s).

The additive(s) may be present in the powder part or the liquid part or the powder part and the liquid part.

The nature and structure of the additive(s) is not particularly limited, either unless the desired result cannot be achieved.

Additives of adjuvants which can be used include accelerators, inhibitors or retarders, stabilizers, pigments, dyes, fluoride release agents, surface tension depressants and wetting aids, antioxidants, and other ingredients well known to those skilled in the art. The amounts and types of each ingredient in the composition should be adjusted to provide the desired physical and handling properties before and after polymerization.

Examples of dyes or pigments, which can be used include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual colouring of the dental compositions.

Examples of photobleachable colorants which can be present include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The colour of the compositions of the invention may be additionally imparted by a sensitizing compound.

Examples of fluoride release agents which can be present include naturally occurring or synthetic fluoride minerals. These fluoride sources can optionally be treated with surface treatment agents.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers).

Further additives, which can be added, include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, and silicone oils), flavorants, anti-microbials, fragrances.

If present, additive(s) are typically present in the following amounts:
    Lower limit: at least 0.05 or at least 0.1 or at least 0.5 wt. %;
    Upper limit: utmost 5 or utmost 3 or utmost 2 wt. %;
    Range: from 0.05 to 5 or from 0.1 to 3 or from 0.5 to 2 wt. %;
wt. % with respect to the whole composition.

According to another embodiment, the hardenable dental resin composition described in the present text is characterized as follows:
comprising a powder part and a liquid part,
    the powder part comprising:
    acid-reactive glass filler A in an amount from 1 to 60 wt. %,
    non acid-reactive nanocluster filler B in an amount from 10 to 80 wt. %,
    oxidizing component(s),
    (thio)barbituric acid component(s),
    sensitizing agent(s),
    transition metal component(s),
    the liquid part comprising:
    polymerizable components with an acidic moiety(s),
    polymerizable components without an acidic moiety(s),
    wherein wt. % refers to the weight of the whole composition.

According to one embodiment, the hardenable dental resin composition described in the present text comprises:
    acid-reactive glass filler A in an amount from 20 to 60 wt. % or from 20 to 40 wt. %,
    non acid-reactive nanocluster filler B in an amount from 20 to 70 wt. % or from 30 to 60 wt. %,
    oxidizing component(s) in an amount from 0.1 to 10 wt. % or from 0.5 to 5 wt. %,
    (thio)barbituric acid component(s) in an amount from 0.1 to 5 wt. % or from 0.5 to 3 wt. %, polymerizable component(s) with an acidic moiety in an amount from 1 to 30 wt. % or from 7 to 20 wt. %, polymerizable component(s) without an acidic moiety in an amount from 1 to 40 wt. % or from 3 to 20 wt. %, sensitizing agent(s) in an amount from 0.005 to 2 wt. % or from 0.05 to 0.5 wt. %, transition metal component in an amount from 0.001 to 1 wt. % or from 0.005 to 0.1 wt. %, sulfinic acid component in an amount from 0 to 5 wt. % or from 0.5 to 2.5 wt. %, additive(s) in an amount from 0 to 5 wt. % or from 0.1 to 2.5 wt. %, wt. % with respect to the weight of the whole composition.

According to another embodiment, the hardenable dental resin composition described in the present text comprises:

acid-reactive glass filler A being a fluoroaluminasilicate glass in an amount from 20 to 60 wt. % or from 20 to 40 wt. %, non acid-reactive surface-treated nanocluster filler B in an amount from 20 to 70 wt. % or from 30 to 60 wt. %, oxidizing component(s) in an amount from 0.1 to 10 wt. % or from 0.5 to 5 wt. %, (thio)barbituric acid component(s) in an amount from 0.1 to 5 wt. % or from 0.5 to 3 wt. %, polymerizable component(s) with an acidic moiety in an amount from 1 to 30 wt. % or from 7 to 20 wt. %, polymerizable component(s) without an acidic moiety in an amount from 1 to 40 wt. % or from 3 to 20 wt. %, sensitizing agent(s) in an amount from 0.005 to 2 wt. % or from 0.05 to 0.5 wt. %, transition metal component in an amount from 0.001 to 1 wt. % or from 0.005 to 0.1 wt. %, sulfinic acid component in an amount from 0.1 to 5 wt. % or from 0.5 to 2.5 wt. %, additive(s) in an amount from 0 to 5 wt. % or from 0.1 to 2.5 wt. %, wt. % with respect to the weight of the whole composition.

The hardenable dental resin composition described in the present text can be produced as follows: The powder part and the liquid part are prepared in separate steps.

The powder part is typically prepared by providing the respective components of the powder part in powder form and mixing the respective powder components, e.g. in a so-called aero wheel (Rhoenrad).

If desired, a milling step for adjusting the particle size of the respective powder components can be conducted.

The obtained mixture is then transferred to a powder filling device, typically equipped with an extruder for transporting the powder mixture to the packaging device, e.g. a dental mixing capsule.

The liquid part is typically prepared by providing the respective components of the liquid part in liquid form and mixing the respective liquid components. Non-liquid parts like for example copper salts can be dissolved in the liquid part.

Described is also a kit of parts comprising the hardenable dental resin composition as described in the present text and one or more of the following items:

dental adhesive;
dental post;
dental milling block;
instruction for use.

A dental adhesive is a material which can be used for adhering the hardenable dental resin composition to the surface of a prepared tooth.

Commercially available dental adhesives which can be used include Scotchbond™ Universal (3M Oral Care).

A dental post is a post which is used in a dental root canal treatment and can help to support the fixing of a dental crown on a prepared tooth stump.

A dental milling block is a block from which dental restorations like dental crowns and bridges can be machined.

The instruction of use typically contains a description of the process steps the practitioner should follow when using the dental resin composition described in the present text.

In particular during storage, the hardenable dental resin composition described in the present text is typically packaged in a suitable packaging device.

According to one embodiment, the powder part and liquid part are contained in separate sealable vessels (e.g. made out of plastic or glass).

For use, the practitioner may take adequate portions of the components from the vessels and mix the portions by hand on a mixing plate.

According to another embodiment, the respective parts are contained in separate compartments of a delivery system.

Thus, the hardenable composition described in the present text may be present in a device for storing and delivery, the device comprising compartment A and compartment B separated from each other during storage and a nozzle connected to either compartment A or compartment B, compartment A containing powder part P and compartment B containing liquid part L, wherein compartment A has a volume in the range of 0.5 to 5 ml or 0.8 to 3 ml and compartment B has a volume in the range of 0.05 to 2 ml or 0.08 to 1 ml.

Other suitable delivery systems are described e.g. in U.S. Pat. No. 6,543,611 B1 (Peuker et al.), U.S. Pat. No. 4,941,751 (Muehlbauer), U.S. Pat. No. 5,088,830 (Muehlbauer), U.S. Pat. No. 6,386,872 (Muasa et al.) or EP 0 783 872 A2 (Voco). The content of these references is herewith incorporated by reference.

The curable composition described in the present text is typically provided to the practitioner with an instruction for use.

The instruction for use typically contains hints how to store the kit of parts, mix the respective parts of the kit of parts and/or how to apply the composition obtained by mixing the parts to the surface of hard dental tissue.

The hardenable dental resin composition described in the present text is typically used as follows:

provide the hardenable dental resin composition,
mix the powder and liquid part of the dental resin composition to obtain a mixture,
apply the mixture to the surface of a tooth or a dental restoration,
optionally apply radiation,
let the mixture harden.

A typical hardening time is from 1 to 10 min or from 1 to 5 min within a temperature range from 20 to 40° C.

The hardenable dental resin composition described in the present text is in particular for use as a self-adhesive dental resin filling material, a self-adhesive fissure sealing material, self-adhesive dental resin core build up material, self-adhesive dental resin cement material, a self-adhesive dental root channel material All components used in the dental composition described in the present text should be sufficiently biocompatible, that is, the composition should not produce a toxic, injurious, or immunological response in living tissue.

According to one embodiment the hardenable dental resin composition described in the present text does not comprising one or more of the following components:

polyacid(s) in an amount of more than 1 wt. %;
complexing agent(s), if added as a separate component, in an amount of more than 1 wt. %;
wt. % with respect to the weight of the whole composition.

Thus, the dental composition described in the present text cannot be regarded as a typical glass ionomer cement (GIZ) or resin-modified glass ionomer cement (RM-GIZ).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized water, and all molecular weights are weight average molecular weight.

Moreover, unless otherwise indicated all experiments were conducted at ambient conditions (23° C.; 1013 mbar).
Methods
Flexural Strength (FS)

If desired, the flexural strength can be measured according to DIN EN ISO 4049:2010-03 with the proviso that the light cured, filled moulds are not stored in a water bath at 37° C. for 15 min, but are demoulded and ground right after light curing.
Compressive Strength (CS)

If desired, the measurement of the compressive strength can be carried out according to the EN-ISO 9917-1:2007 with the proviso that for covering the composition a glass slab is used instead of a foil.

Cylindrical specimens with a diameter of 4 mm and a height of 6 mm are used. Specimens of the materials are prepared at room temperature and 50% relative humidity using split moulds. The moulds are placed on microscope slides and thoroughly filled with the mixed material to avoid incorporation of air bubbles. The filled moulds are covered with another glass slab and fixed in a screw clamp with slight pressure to extrude excess material. The whole assembly is stored at 36° C. and at least 95% relative humidity. 1 h after start of mixing the specimens are removed from the moulds and placed in water at 36° C. 6 specimens are prepared for each material. Materials are measured 24 h after start of mixing. The exact diameter of each specimen is measured prior to the measurement. The strength of the specimen is measured by applying a compressive load using a Zwick universal testing machine (Zwick GmbH & Co. KG, Ulm, Germany) operating at a crosshead speed of 1 mm/min.
Particle Size (Suitable for Micro-Sized Particles)

If desired, the particle size distribution including the mean particle size can be determined with a Mastersizer 3000 (Malvern) particle size detection device. During the measurement, ultrasonic was used to accurately disperse the sample.

Particle Size (Suitable for Nano-Sized Particles)

If desired, particle size measurements can be made using a light scattering particle sizer equipped with a red laser having a 633 nm wavelength of light (obtained under the trade designation "ZETA SIZER—Nano Series, Model ZEN3600" from Malvern Instruments Inc., Westborough, Mass.). Each sample is analyzed in a one-centimeter square polystyrene sample cuvette. The sample is diluted 1:100, e.g. 1 g of sample was given to 100 g of de-ionized water and mixed. The sample cuvette is filled with about 1 gram of diluted sample. The sample cuvette is then placed in the instrument and equilibrated at 25° C. The instrument parameters are set as follows: dispersant refractive index 1.330, dispersant viscosity 0.8872 mPa*s, material refractive index 1.43, and material absorption value 0.00 units. The automatic size-measurement procedure is then run. The instrument automatically adjusts the laser-beam position and attenuator setting to obtain the best measurement of particle size.

The light scattering particle-sizer illuminated the sample with a laser and analyzed the intensity fluctuations of the light scattered from the particles at an angle of 173 degrees. The method of Photon Correlation Spectroscopy (PCS) is used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulative mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

In the scope of this document the Z-average size is referred to as "mean particle size".
Working Time (Ta) and Setting Time (Te)

If desired, the setting behaviour of the prepared glass ionomer cement composition can be determined using a Physica MCR 301 Rheometer (Anton Paar) applying the following parameters:

Oscillating measurement with 8 mm disc on disc set-up; gap 0.75 mm; deformation 1.75%; frequency: 1.25 HZ; temperature: 28° C.

The loss angle (tan delta) is recorded over time and the maximum (ta) and the minimum (te) of the graph determined. The average of two measurements with respect to the maximum and the minimum is given in min:sec.

Materials

TABLE 1

| Name | Description |
|---|---|
| Zr/Si Nanocluster | Nanocluster particles (Preparatory Example A of U.S. Pat. No. 6,730,156 B1 (Windisch et al.)) |
| Ionol | 2,6-ditert.butyl-4-methylphenol |
| BZPBS | 1-Benzyl-5-phenyl-barbituric acid |
| TEGDMA | Triethylenglycoldimethacrylate |
| GDMA | Glyceroldimethacrylate |
| PERSULFAT | Natriumperoxodisulfat |
| NA-TASS | p-Toluenesulfonic acid |
| Calcium hydroxide | Calcium hydroxide |
| Acid reactive filler | Strontium aluminum fluorosilicate glass (D10 1.16 µm; D50 3.71 µm; D90 8.24 µm) |
| Colorants | |
| Precipitated silica | |
| Non-acid reactive filler | Strontium aluminium borosilikate glass GM 32087; silanated (3%); Schott |
| Camphorquinone | camphorquinone |
| Copper acetate monohydrate | Copper(II) acetate monohydrate |
| Methacrylated bisphenol | Bisphenol A bis (3-methacryloyloxypropyl)ether substituted dimethacrylat; CAS 27689-12-9 |
| Methacrylated glycerin phosphate | Mixture of mono-, di- and tri-glycerin-dimethacrylate-ester of phosphoric acid; CAS 1224866-76-5 |

Formulations

TABLE 2

| | Material | Ex 1 | Ex. 2 | C. E. 3 |
|---|---|---|---|---|
| Powder | Persulfat | 1.50 | 1.50 | 1.50 |
| | NA-TSS | 1.125 | 1.125 | 1.125 |
| | Calcium hydroxide | 2.00 | 2.00 | 2.00 |
| | BZPBS | 1.90 | 1.90 | 1.90 |
| | Acid reactive filler | 36.625 | 36.625 | 36.625 |
| | Precipitated silica | 0.10 | 0.10 | 0.10 |
| | Colorants | 1.76 | 1.76 | 1.76 |
| | Zr/Si Nanocluster | 53.18 | 25.00 | — |
| | Non-acid reactive filler | 1.50 | 29.68 | 54.68 |
| Liquid | camphorquinone | 0.12 | 0.12 | 0.12 |
| | Ionol | 0.164 | 0.164 | 0.164 |
| | Copper acetate monohydrate | 0.10 | 0.10 | 0.10 |
| | TEGDMA | 15.00 | 15.00 | 15.00 |
| | Methacrylated bisphenol | 25.00 | 25.00 | 25.00 |
| | Methacrylated glycerin phosphate | 59.58 | 59.58 | 59.58 |

Capsule Filling

A hopper holds the powder to be filled. The bottom of the hopper ends in a funnel. This is the outlet through which the powder parallel part of the auger doses into capsules. The lower parallel flights of the auger within the funnel are machined to a constant pitch so that each pitch has a precise volume. The auger drive rotates the auger at a constant speed to produce a continuous dosing flow. An agitation blade, separately driven and controlled, rotates in the opposite direction to the auger. The agitation blade extends down to the throat of the funnel. Filled capsules are checked for correct filling weight.

Results/Finding

| Material | Ex 1 | Ex. 2 | C. E. 3 |
|---|---|---|---|
| Flexural strength [MPa] | 106 | 110 | 116 |
| properly filled capsules/h | 622 | 484 | 172 |

In FIG. 1 the powder composition of the powder part of the dental resin composition according to Comparative Example 3 was used and filled into a hopper used for filling dental mixing capsules.

As can be seen, the powder composition showed heavy clogging and agglomeration of the powder components due to electrostatic charging which occurred during the mixing and filling process.

Figure 2:
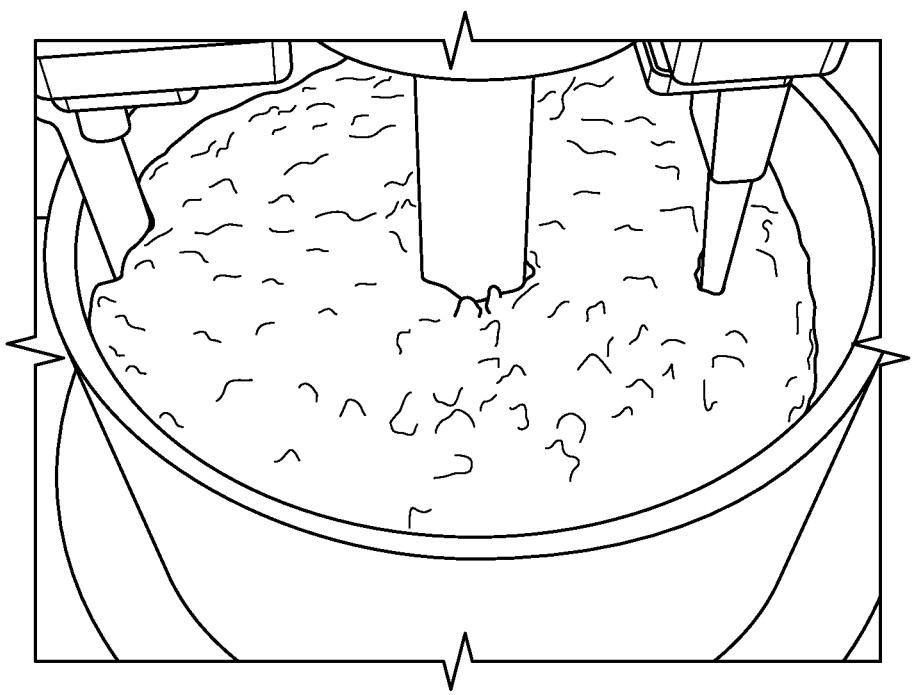
FIG. 2 is a photograph of a vessel used for filling a powder mixture containing non-acid reactive nanocluster filler into a packaging device.

In FIG. 2 the powder composition of the powder part of the dental resin composition according to Inventive Example 1 was used and filled into a hopper used for filling dental mixing capsules.

As can be seen, the clogging and agglomeration of the powder components of the powder composition was reduced and thus enables a more efficient filling process of the dental mixing capsules.

What is claimed is:

1. A hardenable dental resin composition comprising:
   a powder part comprising:
      acid-reactive glass filler A, and
      non acid-reactive nanocluster filler B,
         wherein the non acid-reactive nanocluster filler B is present in an amount that is greater than an amount of acid-reactive glass filer A present;
   a liquid part comprising:
      polymerizable components with an acidic moiety, and
      polymerizable components without an acidic moiety; and
   a dual-cure initiator system comprising:
      sensitizing agent(s),
      oxidizing component(s),
      (thio)barbituric acid component(s), and
      transition metal component(s);
   wherein the sensitizing agent(s), oxidizing component(s), (thio)barbituric acid component(s), and transition metal component(s) are distributed amongst the powder part and the liquid part,
   wherein the powder part and the liquid part together form the hardenable dental resin composition, and
   wherein the hardenable dental resin composition is self-adhesive.

2. The hardenable dental resin composition according to claim 1, wherein:
   the powder part comprises:
      the oxidizing component(s), and
      the (thio)barbituric acid component(s); and
   the liquid part comprises:
      the sensitizing agent(s), and
      the transition metal component(s).

3. The hardenable dental resin composition according claim 1, wherein the acid-reactive glass filler A is characterized by one or more of the following features:
   being surface treated;
   mean particle size: from 3 to 10 µm;
   d90/µm: from 6 µm to 15 µm;
   specific surface: from 50 to 400 $m^2/g$; and
   being a fluoroaluminosilicate glass.

4. The hardenable dental resin composition according to claim 1, wherein the non acid-reactive nanocluster filler B is characterized by:
   being surface treated;
   Specific surface: from 50 to 400 $m^2/g$;
   average particle diameter of primary particles: from 5 to 100 nm; or
   comprising particles of $SiO_2$, $ZrO_2$ and mixtures thereof.

5. The hardenable dental resin composition according to claim 1, wherein the powder part and the liquid part are in a ratio from 1:1 to 6:1 with respect to weight.

6. The hardenable dental resin composition according to claim 1, wherein the polymerizable components with an acidic moiety is represented by formula (I):

$$A_nBC_m \quad (I),$$

wherein:
B is selected from (i) linear or branched $C_1$ to $C_{12}$ alkyl, optionally substituted with functional groups, (ii) $C_6$ to $C_{12}$ aryl, optionally substituted with functional groups, or (iii) organic group having 4 to 20 carbon atoms bonded to one another by one or more ether, thioether, ester, thioester, thiocarbonyl, amide, urethane, carbonyl and/or sulfonyl linkages;
A an ethylenically unsaturated group;
C is an acidic group;
m and n are independently 1, 2, 3, 4, 5 or 6;
wherein the acidic group comprises one or more carboxylic acid residues, phosphoric acid residues, phosphonic acid residues, or sulphonic acid residues.

7. The hardenable dental resin composition according to claim 1, wherein the oxidizing component is selected from peroxides, peroxodisulfate, peroxodiphosphate, and combinations thereof.

8. The hardenable dental resin composition according to claim 1, wherein the sensitizing agent comprises an alpha di-keto moiety, an anthrachinone moiety, a thioxanthone moiety, or a benzoin moiety.

9. The hardenable dental resin composition according to claim 1, wherein the transition metal component is selected from salt(s) of titanium, vanadium, chromium, manganese, iron, cobalt, nickel, or copper.

10. The hardenable dental resin composition according to claim 1, comprising:
the acid-reactive glass filler A in an amount from 1 to 60 wt. %,
the non acid-reactive nanocluster filler B in an amount from 10 to 80 wt. %,
the polymerizable component(s) with an acidic moiety in an amount from 1 to 30 wt. %,
the polymerizable component(s) without an acidic moiety in an amount from 1 to 40 wt. %,
the sensitizing agent(s) in an amount from 0.005 to 2 wt. %,
the oxidizing component in an amount from 0.1 to 10 wt. %,
the (thio)barbituric acid component(s) in an amount from 0.1 to 5 wt. %,
the transition metal component(s) in an amount from 0.001 to 1 wt. %,
additive(s) in an amount from 0 to 5 wt. %,
wherein each wt. % is with respect to the weight of the hardenable dental resin-composition.

11. The hardenable dental resin composition according to claim 1, further comprising one or more of:
a polyacid in an amount no more than 1 wt. %; and
a complexing agent in an amount no more than 1 wt. %;
wherein each wt. % is with respect to the weight of the hardenable dental resin composition.

12. The hardenable dental resin composition according to claim 1, being in the form of a self-adhesive dental resin filling material, a self-adhesive dental resin core build up material, a self-adhesive dental resin cement material, a self-adhesive fissure sealing material, or a self-adhesive dental root channel material.

13. The hardenable dental resin composition according to claim 1, for use in a process comprising the steps of:
mixing the powder part and the liquid part to obtain a mixture,
applying the mixture to a tooth surface or a dental restoration.

14. A kit of parts comprising: the hardenable dental resin composition according to claim 1, and one or more of:
a dental adhesive;
a dental post; and
a dental milling block.

15. The hardenable dental resin composition according to claim 1, wherein the non acid-reactive nanocluster filler B reduces the electrical charging of the powder part components.

16. The hardenable dental resin composition according to claim 6, wherein the acidic group comprises one or more residues selected from —COOH, —CO—O—CO—, —O—P(O)(OH)OH, —P(O)(OH)OH, and —SO$_3$H.

17. The hardenable dental resin composition according to claim 1, comprising:
the non acid-reactive nanocluster filler B in an amount from 10 to 80 wt. % with respect to the weight of the hardenable dental resin composition.

18. The hardenable dental resin composition according to claim 1, the powder further comprising strontium aluminium borosilicate.

19. The hardenable dental resin composition according to claim 1, wherein the acid-reactive glass filler A is strontium aluminium fluorosilicate.

20. The hardenable dental resin composition according to claim 1, wherein the polymerizable components without an acidic moiety is represented by formula (II):

$$A_nBA_m \quad (II),$$

wherein:
A is an ethylenically unsaturated group;
B is selected from (i) linear or branched $C_1$ to $C_{20}$ alkyl, optionally substituted with —Cl, —Br, —I, —OH, or combinations thereof; (ii) $C_6$ to $C_{12}$ aryl, optionally substituted with —Cl, —Br, —I, —OH, or combinations thereof; or (iii) organic group having 4 to 20 carbon atoms bonded to one another by one or more ether, thioether, ester, thioester, thiocarbonyl, amide, urethane, carbonyl and/or sulfonyl linkages;
m and n are independently selected from 0, 1, 2, 3, 4, 5 or 6;
provided n is at least 1.

* * * * *